United States Patent
Sherwood

(10) Patent No.: US 8,725,252 B2
(45) Date of Patent: May 13, 2014

(54) ELECTRIC ENERGY STORAGE DEVICE ELECTRODE INCLUDING AN OVERCURRENT PROTECTOR

(75) Inventor: Gregory J. Sherwood, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 499 days.

(21) Appl. No.: 12/968,584

(22) Filed: Dec. 15, 2010

(65) Prior Publication Data

US 2011/0152961 A1 Jun. 23, 2011

Related U.S. Application Data

(60) Provisional application No. 61/288,098, filed on Dec. 18, 2009.

(51) Int. Cl.
*A61N 1/39* (2006.01)
*H01G 2/14* (2006.01)
*H01G 9/052* (2006.01)

(52) U.S. Cl.
USPC ............... 607/5; 29/25.03; 361/503; 361/534

(58) Field of Classification Search
USPC ........................................................ 361/534
See application file for complete search history.

(56) References Cited

U.S. PATENT DOCUMENTS

| | | | |
|---|---|---|---|
| 2,636,076 A | 4/1953 | Odvar et al. | |
| 3,025,441 A | 3/1962 | West | |
| 3,331,759 A | 7/1967 | Middelhoek et al. | |
| 3,445,731 A | 5/1969 | Saeki et al. | |
| 3,627,520 A | 12/1971 | Rogers | |
| 3,638,083 A * | 1/1972 | Dornfeld et al. | 361/321.1 |
| 3,644,796 A | 2/1972 | Carino | |
| 3,647,415 A | 3/1972 | Yano et al. | |

(Continued)

FOREIGN PATENT DOCUMENTS

| | | |
|---|---|---|
| EP | 0877400 A1 | 11/1998 |
| EP | 1470267 B1 | 4/2009 |

(Continued)

OTHER PUBLICATIONS

Bocek, Joseph M, et al., "Method and Apparatus for Charging Partitioned Capacitors", U.S. Appl. No. 11/462,301, filed Aug. 3, 2006, 53 pgs.

(Continued)

*Primary Examiner* — Kennedy Schaetzle
(74) *Attorney, Agent, or Firm* — Schwegman Lundberg & Woessner, P.A.

(57) ABSTRACT

One embodiment includes a capacitor case sealed to retain electrolyte, at least one electrode disposed in the capacitor case, the at least one electrode comprising an overcurrent protector, a conductor coupled to the overcurrent protector and in electrical communication with a remainder of the electrode, the conductor sealingly extending through the capacitor case to a terminal disposed on an exterior of the capacitor case, a second electrode disposed in the capacitor case, a separator disposed between the electrode and the second electrode and a second terminal disposed on the exterior of the capacitor case and in electrical communication with the second electrode, with the terminal and the second terminal electrically isolated from one another, wherein the overcurrent protector is to interrupt electrical communication between the terminal and the remainder of the electrode at a selected current level.

19 Claims, 10 Drawing Sheets

(56) References Cited

U.S. PATENT DOCUMENTS

| | | | |
|---|---|---|---|
| 3,789,502 A | 2/1974 | Callins et al. | |
| 4,059,116 A | 11/1977 | Adams | |
| 4,085,397 A | 4/1978 | Yagher | |
| 4,107,762 A * | 8/1978 | Shirn et al. | 361/534 |
| 4,118,753 A | 10/1978 | Vind | |
| 4,406,286 A | 9/1983 | Stein | |
| 4,442,473 A | 4/1984 | Holtzman et al. | |
| 4,635,163 A | 1/1987 | Voglaire | |
| 4,687,951 A | 8/1987 | McElroy | |
| 4,720,767 A * | 1/1988 | Chan et al. | 361/275.4 |
| 4,840,122 A | 6/1989 | Nerheim | |
| 4,882,115 A * | 11/1989 | Schmickl | 361/538 |
| 4,894,746 A | 1/1990 | Mori et al. | |
| 5,062,025 A | 10/1991 | Verhoeven et al. | |
| 5,097,404 A | 3/1992 | Layh | |
| 5,115,378 A | 5/1992 | Tsuchiya et al. | |
| RE34,879 E | 3/1995 | Bocchi et al. | |
| 5,424,909 A | 6/1995 | Kuriyama | |
| 5,468,254 A | 11/1995 | Hahn et al. | |
| 5,591,211 A | 1/1997 | Meltzer | |
| 5,591,217 A | 1/1997 | Barreras | |
| 5,634,938 A | 6/1997 | Swanson et al. | |
| 5,660,737 A | 8/1997 | Elias et al. | |
| 5,763,911 A * | 6/1998 | Matthews et al. | 257/301 |
| 5,807,397 A | 9/1998 | Barreras | |
| 5,874,770 A | 2/1999 | Saia et al. | |
| 5,930,109 A | 7/1999 | Fishler | |
| 6,115,235 A | 9/2000 | Naito | |
| 6,141,205 A | 10/2000 | Nutzman et al. | |
| 6,161,040 A | 12/2000 | Blunsden | |
| 6,193,779 B1 | 2/2001 | Reichert et al. | |
| 6,219,221 B1 | 4/2001 | Kibi et al. | |
| 6,241,751 B1 | 6/2001 | Morgan et al. | |
| 6,310,757 B1 | 10/2001 | Tuzuki et al. | |
| 6,347,032 B2 | 2/2002 | Naito | |
| 6,350,406 B1 | 2/2002 | Satou et al. | |
| 6,351,371 B1 | 2/2002 | Yoshida et al. | |
| 6,385,031 B1 | 5/2002 | Lerche et al. | |
| 6,456,877 B1 | 9/2002 | Fishler | |
| 6,459,566 B1 | 10/2002 | Casby et al. | |
| 6,493,212 B1 | 12/2002 | Clarke et al. | |
| 6,509,588 B1 | 1/2003 | Barr et al. | |
| 6,560,089 B2 | 5/2003 | Miltich et al. | |
| 6,678,559 B1 | 1/2004 | Breyen et al. | |
| 6,687,118 B1 | 2/2004 | O'Phelan et al. | |
| 6,699,265 B1 | 3/2004 | O'Phelan et al. | |
| 6,775,127 B2 * | 8/2004 | Yoshida | 361/528 |
| 6,778,860 B2 | 8/2004 | Ostroff et al. | |
| 6,785,123 B2 | 8/2004 | Keser | |
| 6,801,424 B1 * | 10/2004 | Nielsen et al. | 361/517 |
| 6,807,048 B1 | 10/2004 | Nielsen et al. | |
| 6,850,405 B1 | 2/2005 | Mileham et al. | |
| 6,855,234 B2 | 2/2005 | D'Astolfo, Jr. | |
| 6,865,417 B2 | 3/2005 | Rissmann et al. | |
| 6,914,769 B2 | 7/2005 | Welsch et al. | |
| 6,952,608 B2 | 10/2005 | Ostroff | |
| 6,954,670 B2 | 10/2005 | Ostroff | |
| 7,024,246 B2 | 4/2006 | Acosta et al. | |
| 7,327,557 B2 | 2/2008 | Poplett | |
| 7,522,957 B2 | 4/2009 | Ostroff | |
| 7,531,010 B1 | 5/2009 | Feger et al. | |
| 7,564,677 B2 | 7/2009 | Poplett | |
| 7,760,488 B2 | 7/2010 | Breznova et al. | |
| 7,856,265 B2 | 12/2010 | Linder et al. | |
| 8,179,663 B2 | 5/2012 | Brabeck et al. | |
| 2003/0169560 A1 | 9/2003 | Welsch et al. | |
| 2004/0147960 A1 | 7/2004 | O'Phelan et al. | |
| 2004/0147961 A1 | 7/2004 | O'Phelan et al. | |
| 2004/0240155 A1 | 12/2004 | Miltich et al. | |
| 2005/0017888 A1 | 1/2005 | Sherwood et al. | |
| 2006/0035152 A1 | 2/2006 | Nishimura et al. | |
| 2006/0139580 A1 | 6/2006 | Conner | |
| 2006/0139850 A1 | 6/2006 | Rorvick et al. | |
| 2006/0166088 A1 | 7/2006 | Hokanson et al. | |
| 2006/0174463 A1 | 8/2006 | O'Phelan et al. | |
| 2006/0249774 A1 | 11/2006 | Sherwood | |
| 2007/0109723 A1 * | 5/2007 | Kuriyama et al. | 361/502 |
| 2007/0109727 A1 | 5/2007 | Edson et al. | |
| 2007/0188980 A1 | 8/2007 | Hossick-Schott | |
| 2008/0030927 A1 | 2/2008 | Sherwood | |
| 2008/0170354 A1 * | 7/2008 | Dvorak et al. | 361/524 |
| 2008/0198534 A1 | 8/2008 | Lee et al. | |
| 2008/0208270 A1 | 8/2008 | Linder et al. | |
| 2009/0231782 A1 | 9/2009 | Fujita et al. | |
| 2009/0237862 A1 | 9/2009 | Nielsen et al. | |
| 2009/0242415 A1 | 10/2009 | Yoshimitsu | |
| 2009/0273884 A1 | 11/2009 | Shimizu et al. | |
| 2010/0010562 A1 * | 1/2010 | Daley et al. | 607/37 |
| 2010/0110614 A1 | 5/2010 | Umemoto et al. | |
| 2010/0110615 A1 | 5/2010 | Nishimura et al. | |
| 2010/0157510 A1 | 6/2010 | Miyachi et al. | |
| 2010/0193731 A1 | 8/2010 | Lee et al. | |
| 2010/0195261 A1 | 8/2010 | Sweeney et al. | |
| 2010/0226066 A1 | 9/2010 | Sweeney et al. | |
| 2010/0226070 A1 | 9/2010 | Yang et al. | |
| 2011/0038098 A1 | 2/2011 | Taira et al. | |
| 2011/0149474 A1 | 6/2011 | Sherwood et al. | |
| 2011/0149475 A1 | 6/2011 | Sherwood et al. | |
| 2011/0152958 A1 | 6/2011 | Sherwood et al. | |
| 2011/0152959 A1 * | 6/2011 | Sherwood et al. | 607/5 |
| 2011/0152960 A1 | 6/2011 | Daley et al. | |
| 2011/0317370 A1 | 12/2011 | Sherwood | |
| 2013/0141842 A1 | 6/2013 | Sherwood et al. | |

FOREIGN PATENT DOCUMENTS

| | | |
|---|---|---|
| JP | 02087512 A | 3/1990 |
| JP | 04354114 A | 12/1992 |
| WO | WO-2006139850 A1 | 6/2006 |
| WO | WO-2011075506 A2 | 6/2011 |
| WO | WO-2011075506 A3 | 6/2011 |
| WO | WO-2011075508 A2 | 6/2011 |
| WO | WO-2011075508 A3 | 6/2011 |
| WO | WO-2011075511 A2 | 6/2011 |
| WO | WO-2011075511 A3 | 6/2011 |

OTHER PUBLICATIONS

"U.S. Appl. No. 12/968,555, Notice of Allowance mailed Apr. 2, 2013", 9 pgs.

"U.S. Appl. No. 12/968,555, Notice of Allowance mailed Nov. 23, 2012", 9 pgs.

"U.S. Appl. No. 12/968,555, Response filed Oct. 29, 2012 to Restriction Requirement mailed Sep. 27, 2012", 7 pgs.

"U.S. Appl. No. 12/968,555, Restriction Requirement mailed Sep. 27, 2012", 7 pgs.

"U.S. Appl. No. 12/968,555, Supplemental Notice of Allowability mailed Dec. 26, 2012", 2 pgs.

"U.S. Appl. No. 12/968,571 , Response filed Apr. 3, 2013 to Non Final Office Action mailed Nov. 9, 2012", 13 pgs.

"U.S. Appl. No. 12/968,571, Non Final Office Action mailed Nov. 9, 2012", 15 pgs.

"International Application Serial No. PCT/US2010/060432, Corrected International Preliminary Report on Patentability mailed May 11, 2012", 22 pgs.

"International Application Serial No. PCT/US2010/060432, International Preliminary Report on Patentability mailed Apr. 27, 2012", 16 pgs.

"International Application Serial No. PCT/US2010/060432, Invitation to Pay Additional Fees mailed Sep. 13, 2011", 9 pgs.

"International Application Serial No. PCT/US2010/060432, Search Report mailed Dec. 5, 2011", 6 pgs.

"International Application Serial No. PCT/US2010/060432, Written Opinion mailed Dec. 5, 2011", 14 pgs.

"International Application Serial No. PCT/US2010/060437, Search Report mailed Sep. 13, 2011", 4 pgs.

"International Application Serial No. PCT/US2010/060437, Written Opinion mailed Sep. 13, 2011", 6 pgs.

"International Application Serial No. PCT/US2010/060444, International Preliminary Report on Patentability mailed Jun. 28, 2012", 8 pgs.

(56) References Cited

OTHER PUBLICATIONS

"International Application Serial No. PCT/US2010/060444, International Search Report mailed Sep. 14, 2011", 4 pgs.

"International Application Serial No. PCT/US2011/060444, Written Opinion mailed Sep. 14, 2011", 7 pgs.

"U.S. Appl. No. 12/968,523, Response filed Sep. 23, 2013 to Non Final Office Action mailed Jun. 21, 2013", 8 pgs.

"U.S. Appl. No. 12/968,523, Non Final Office Action mailed Jun. 21, 2013", 12 pgs.

"U.S. Appl. No. 12/968,523, Non Final Office Action mailed Oct. 15, 2013", 9 pgs.

"U.S. Appl. No. 12/968,536, Response filed Sep. 23, 2013 to Non Final Office Action mailed Jun. 21, 2013", 7 pgs.

"U.S. Appl. No. 12/968,536, Non Final Office Action mailed Jun. 21, 2013", 7 pgs.

"U.S. Appl. No. 12/968,536, Non Final Office Action mailed Oct. 2, 2013", 17 pgs.

"U.S. Appl. No. 12/968,555, Notice of Allowance mailed Aug. 28, 2013", 8 pgs.

"U.S. Appl. No. 12/968,561, Response filed Jul. 31, 2013 to Restriction Requirement mailed Jun. 21, 2013", 7 pgs.

US 8,503,164, Aug. 2013, Sherwood et al. (withdrawn).

"U.S. Appl. No. 12/968,561, Response filed Sep. 30, 2013 to Restriction Requirement mailed Aug. 29, 2013", 7 pgs.

"U.S. Appl. No. 12/968,561, Restriction Requirement mailed Jun. 21, 2013", 6 pgs.

"U.S. Appl. No. 12/968,561, Restriction Requirement mailed Aug. 29, 2013", 7 pgs.

"U.S. Appl. No. 12/968,571, Advisory Action mailed Aug. 22, 2013", 3 pgs.

"U.S. Appl. No. 12/968,571, Final Office Action mailed Jun. 3, 2013", 14 pgs.

"U.S. Appl. No. 12/968,571, Non Final Office Action mailed Sep. 13, 2013", 15 pgs.

"U.S. Appl. No. 12/968,571, Response filed Jul. 31, 2013 to Final Office Action mailed Jun. 3, 2013", 11 pgs.

"U.S. Appl. No. 13/165,363, Non Final Office Action mailed Jul. 19, 2013", 18 pgs.

\* cited by examiner

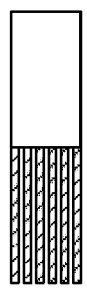
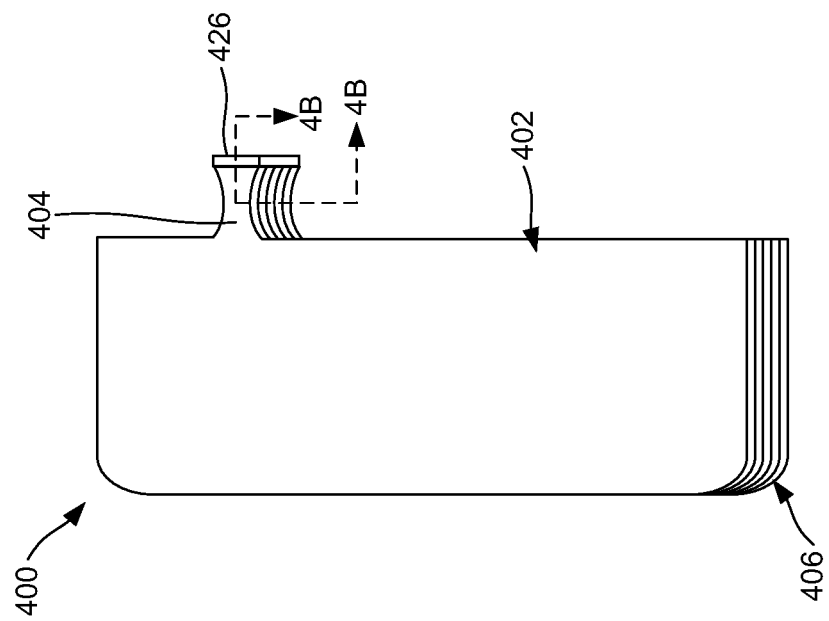

ELECTRIC ENERGY STORAGE DEVICE ELECTRODE INCLUDING AN OVERCURRENT PROTECTOR

CROSS-REFERENCE TO RELATED APPLICATIONS

This application claims the benefit of U.S. Provisional Application No. 61/288,098, filed on Dec. 18, 2009, under 35 U.S.C. §119(e), which is incorporated herein by reference in its entirety.

TECHNICAL FIELD

This document relates generally to energy storage and particularly to sintered electrodes to store energy in an implantable medical device.

BACKGROUND

Capacitors both store and discharge electrical energy quickly. In storing or discharging electrical energy, electrical energy is transferred through the subcomponents of the capacitor. Transferring energy at high rates can stress these components, can damage them and can even destroy them. To address these concerns, systems and methods to protect the capacitor are desired.

SUMMARY

This disclosure relates to apparatus and methods for energy storage devices including overcurrent protectors such as fuses or fusible links. An apparatus according to one embodiment includes a first and second electrode disposed in a capacitor case sealed to retain electrolyte. At least one of the electrodes includes an overcurrent protector to interrupt electrical communication between the electrode and a terminal at a selected current level. In an embodiment, a separator is disposed between the first and second electrode.

An aspect of this disclosure includes a method for making a capacitor having a overcurrent protector. An embodiment according to the method includes forming a first electrode including a connection member comprising an overcurrent protector, coupling the overcurrent protector to a first electrode, stacking a separator onto the first electrode, stacking a second electrode onto the separator, and disposing the first electrode, the separator, the second electrode and overcurrent protector into a capacitor case. The method includes electrically coupling the first electrode and the electrode pose to a first terminal disposed on an exterior of the capacitor case, electrically coupling the second electrode to a second terminal disposed on the exterior of the capacitor case, the second terminal electrically isolated from the first terminal, filling the capacitor case with an electrolyte, and sealing the electrolyte in the capacitor case. Additional embodiments disclose systems including various embodiments of the apparatus.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 4A is a perspective view of capacitor stack with multiple overcurrent protectors, according to various embodiments.

FIG. 4B is a cross section taken along line 4B-4B in FIG. 4A.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This application is for energy storage devices such as capacitors that include overcurrent protection. Some of the embodiments disclosed here couple a overcurrent protector internal to the capacitor to an electrode of the capacitor so that energy stored in or discharged from the electrode is protected from overcurrent. Protecting the electrode reduces or prevents overcurrent from the electrode to a terminal of the energy storage device, such as a terminal coupled to other electronics. Fusing also reduces or prevents overcurrent to the electrode from such electronics.

Various embodiments form a overcurrent protector from electrode material, such as by reducing a portion of the electrode to having a reduced cross section to melt or "blow" when high currents travel through that portion. Some examples include sintered material formed on a substrate, with the sintered material configured to blow. In some examples, an overcurrent protector is disposed in the energy storage device case. With overcurrent protection disposed in cases, an added measure of protection is built into the energy storage device, thereby reducing thermal anomalies associated with the energy storage device, such as those caused by breakdown or related to failure of a device coupled to the energy storage device.

Figure 1:
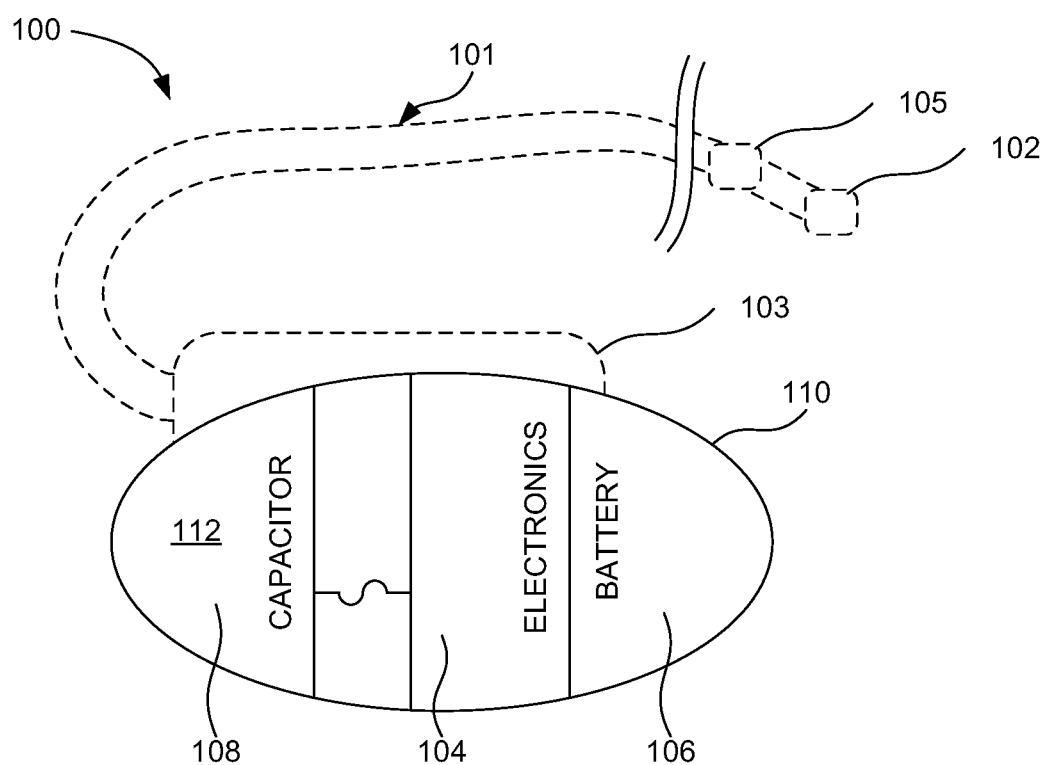
FIG. 1 is a schematic of a medical system including a sintered capacitor, according to some embodiments.

FIG. 1 is a schematic of a system 100 such as a medical system including a sintered capacitor, according to some embodiments. The system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators.

In various embodiments, electronics 104 are to monitor the patient, such as by monitoring a sensor 105, and to monitor and control activity within the system 100. In some examples, the electronics 104 are to monitor a patient, diagnose a condition to be treated such as an arrhythmia, and control delivery of a stimulation pulse of energy to the patient. In some instances, electronics 104 are powered wirelessly using an inductor. In additional configurations, the electronics 104 are powered by a battery 106. In some examples, electronics 104 are to direct small therapeutic bursts of energy from the battery 106 to a patient.

For therapies that use energy discharge rates exceeding what battery 106 is able to provide, such as defibrillation, a capacitor 108 is used. Energy from the battery 106 is controlled by the electronics 104 to charge the capacitor 108. The capacitor 108 is controlled with the electronics 104 to discharge to a patient to treat the patient. In some examples, the capacitor 108 completely discharges to a patient, and in additional examples is switched on to provide therapeutic energy and switched off to truncate therapy delivery.

Some examples of a system 100 include an optional lead system 101. In certain instances, after implantation, the lead system 101 or a portion of the lead system 101 is in electrical communication with tissue to be stimulated. For example, some configurations of lead system 101 contact tissue with a stimulation electrode 102. The lead system 101 couples to other portions of the system 100 via a connection in a header 103. Examples of the system 101 use different numbers of stimulation electrodes and/or sensors in accordance with the needs of the therapy to be performed.

Additional examples function without a lead 101 and are leadless. Leadless examples are positioned in contact with the tissue to be stimulated, or are positioned proximal to a tissue to be stimulated to shock the tissue through intermediary tissue. In some examples, leadless systems are easier to implant and are less expensive as they do not use additional lead components. The housing 110 is used as an electrode in leadless configurations, in some examples.

In certain embodiments, the electronics 104 include an electronic cardiac rhythm management circuit coupled to the battery 106 and the capacitor 108 to discharge the capacitor 108 to provide a therapeutic defibrillation pulse. In some examples, the system 100 includes an anode and a second electrode such as a cathode sized to deliver a defibrillation pulse of at least approximately 50 joules. This energy level is predetermined to achieve a delivered energy level mandated by a governing body or standard associated with a geographic region, such as a European country. In an additional embodiment, the anode and second electrode are sized to deliver a defibrillation pulse of at least approximately 60 joules. This energy level is predetermined to achieve an energy level mandated by a governing body of another region, such as the United States. In some examples, electronics 104 are to control discharge of a defibrillation pulse so that the medical system 100 delivers only the energy mandated by the region in which the system 100 is used.

Packaging anodes and cathodes can reduce their efficiency. Interconnections between conductors coupled to electronics and to the electrodes of the capacitor 108 decrease efficiency of charging and discharging, for example. Accordingly, anodes and cathodes are sized to compensate for decreases in efficiency. As such, in some embodiments, the capacitor 108 includes anodes and second electrodes sized and packaged to deliver a defibrillation pulse of at last approximately 50 joules. Some are sized and packaged to deliver a defibrillation pulse of at least approximately 60 joules.

One characteristic of some sintered electrode examples is that at least one anode and at least one cathode have a DC capacitance that is approximately 23% greater than an AC capacitance for the at least one anode and the second electrode. In some examples, the at least one anode and the second electrode have an AC capacitance of at least 96.7 microfarads per cubic centimeter at 445 total voltage. This is a 30% improvement over an etched capacitor that has 74.5 microfarads per cubic centimeter. Total voltage is the voltage that allows 1 milliamp of leakage per square centimeter. Some examples are aged to 415 volts.

In certain examples, the capacitor 108 includes a capacitor case 112 sealed to retain electrolyte. In some examples, the capacitor case 112 is welded. In some instances, the capacitor case 112 is hermetically sealed. In additional examples, the capacitor case 112 is sealed to retain electrolyte, but is sealed with a seal to allow flow of other matter, such as gaseous diatomic hydrogen or a helium molecule. Some of these examples use an epoxy seal. Several materials can be used to form case 112, including, but not limited to, aluminum, titanium, stainless steel, nickel, a polymeric material, or combinations of these materials. The case 112 is sealed to retain electrolyte. Various electrolytes can be used including, but not limited to, Suzuki-Techno Corporation electrolyte model 1184. The case 112 includes a seal, such as a resin based seal including but not limited to epoxy, in some examples. Some examples include a rubber seal to seal case portions to one another, or to seal subcomponents such as a feedthrough to one or more case portion. In some examples, case 112 is welded together from subcomponents. Some examples include a case that includes one or more backfill ports, but the present subject matter is not so limited.

A hermetically sealed device housing 110 is used to house components, such as the battery 106, the electronics 104, and the capacitor 108. Hermeticity is provided by welding components into the hermetically sealed device housing 110 in some examples. Other examples bond portions of the housing 110 together with an adhesive such as a resin based adhesive such as epoxy. Accordingly, some examples of the housing 110 include an epoxy sealed seam or port. Several materials can be used to form housing 110, including, but not limited to, titanium, stainless steel, nickel, a polymeric material, or combinations of these materials. In various examples, the housing 110 and the case 112 are biocompatible.

The capacitor 108 is improved by the present electrode technology in part because it can be made smaller and with less expense. The improvement provided by these electrodes is pertinent to any application where high-energy, high-voltage, or space-efficient capacitors are desirable, including, but not limited to capacitors used for photographic flash equipment. In other words, present subject matter extends to energy storage devices that benefit from high surface area sintered electrodes including, but not limited to, aluminum. The electrodes described here can be incorporated into cylindrical capacitors that are wound, in addition to stacked capacitors.

Figure 2:
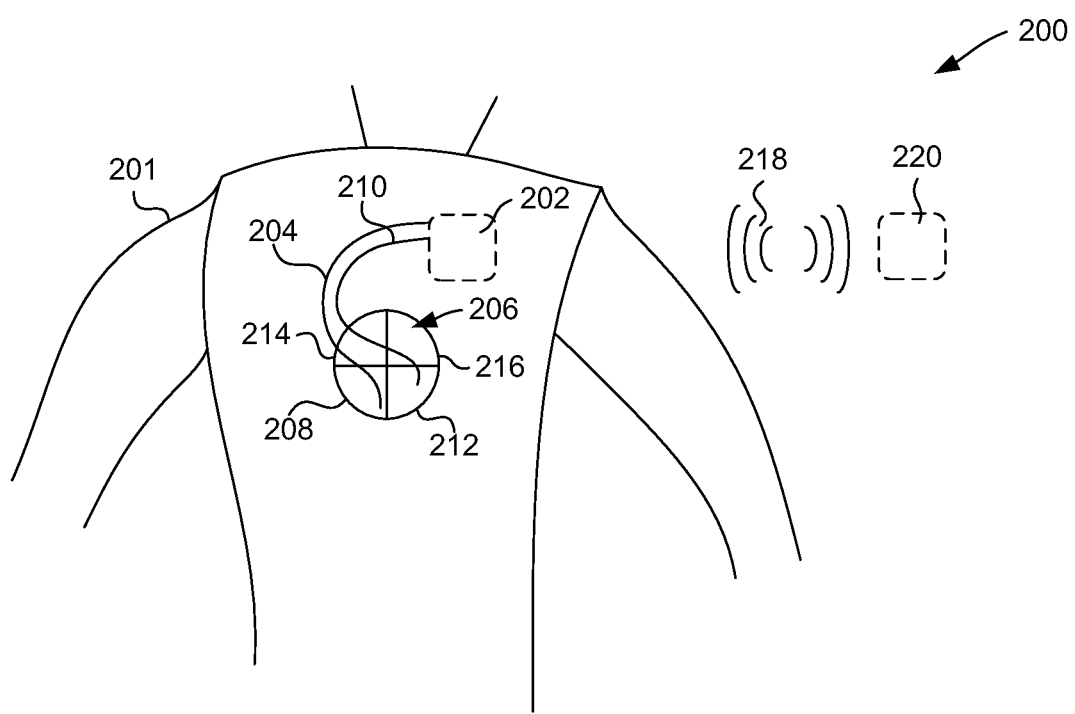
FIG. 2 is an implanted medical system including a sintered capacitor, according to some embodiments.

FIG. 2 is an implanted medical system 200, implanted in a patient 201, and including overcurrent protection, according to some embodiments. The system includes a cardiac rhythm management device 202 coupled to a first lead 204 to extend through the heart 206 to the right ventricle 208 to stimulate at least the right ventricle 208. The system also includes a second lead 210 to extend through the heart 206 to the left ventricle 212. In various embodiments, one or both of the first lead 204 and the second lead 210 include electrodes to sense intrinsic heart signals and to stimulate the heart. The first lead 204 is in direct contact (e.g., touching) with the right atrium 214 and the right ventricle 208 to sense and/or stimulate both of those tissue regions. The second lead 210 is in direct contact with the right atrium 216 and the right ventricle 212 to sense and/or stimulate both those tissue regions. The cardiac rhythm management device 202 uses the lead electrodes to deliver energy to the heart, between electrodes on the leads or between one or more lead electrodes and the cardiac rhythm management device 202. In some examples, the cardiac rhythm management device 202 is programmable and wirelessly communicates 218 programming information with a programmer 220. In some examples, the programmer 220 wirelessly 218 charges an energy storage device of the cardiac rhythm management device 202. Other stimulation topologies, such as those that stimulate other portions of the body, additionally benefit from overcurrent protection disclosed herein.

Figure 3B:
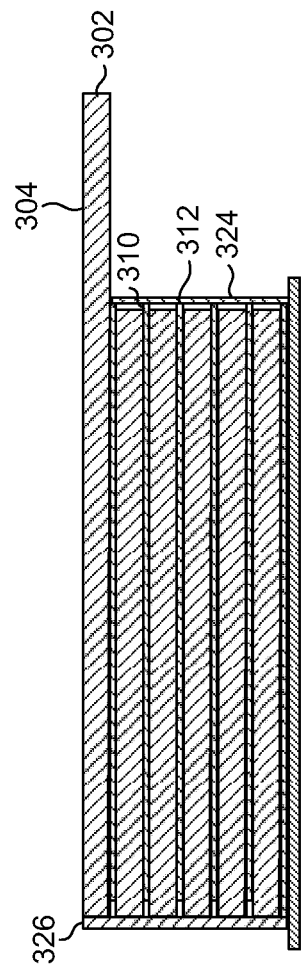
FIG. 3B is a partial cross section taken along line 3B-3B in FIG. 3A.
Figure 3A:
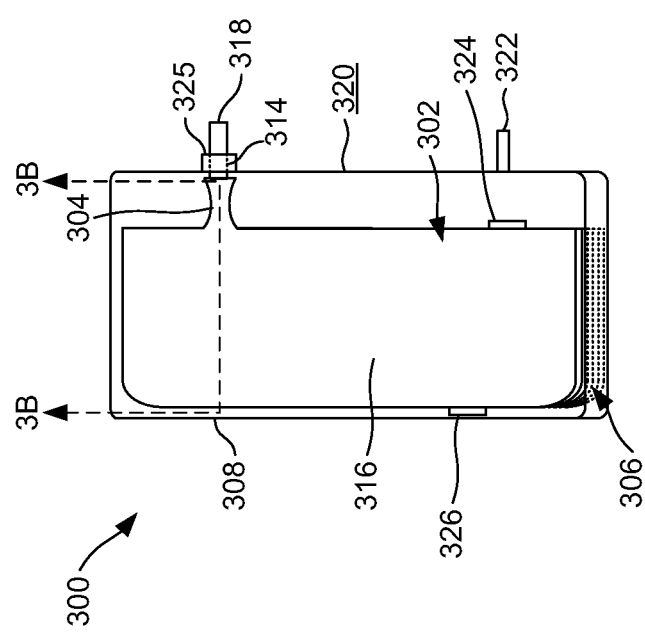
FIG. 3A is a perspective view of an energy storage device including a overcurrent protector, according to various embodiments.

FIG. 3A is a perspective view of a portion of energy storage device 300 including a overcurrent protector, according to various embodiments. FIG. 3B is a partial cross section taken along line 3B-3B in FIG. A. Various examples include a capacitor case 308. In various examples, the capacitor case 308 is sealed to retain electrolyte. Examples of seals include welds, gasketed seals such as those using o-rings, adhesives and other seals. In some examples the case 308 includes a dish portion and a lid portion.

Various examples include at least one electrode 302 disposed in a capacitor case 308. Electrodes contemplated include anodes and cathodes for a capacitor. The present subject matter extends to wound capacitors as well as capacitors with a stack of layers such as flat layers or sheets. In some examples, the at least one electrode 302 includes an overcurrent protector 304 that is formed from the electrode 302. Forming the overcurrent protector 304 includes, in some embodiments, removing material from the electrode 302, such as by cutting the electrode or grinding the electrode. In some examples, the overcurrent protector and the electrode are formed by an operation such as a stamping operation.

An overcurrent protector 304, such as a fuse or fusible link, is coupled to the capacitor case 308 in some examples. In certain instances, the case 308 has the polarity of the electrode protected by the overcurrent protector 304, however such a configuration causes a portion of the electrode (the case) to not be protected by the overcurrent protector 304. This portion is able to conduct energy with the terminal 318.

Various embodiments include a conductor 314 coupled to the overcurrent protector 304 and in electrical communication with a remainder 316 of the electrode 302. In some examples, the conductor 314 sealingly extends through the capacitor case 308 to a terminal 318 disposed on an exterior 320 of the capacitor case 308. Various embodiments include a feedthrough 325 to facilitate the conductor 314 sealingly extending through the case 308. Examples of feedthroughs include glass feedthroughs, adhesive feedthroughs including those with cured resin such as epoxy, and feedthroughs that include a metal eye weldable to the case 308. Some examples include an interconnect 326 to place multiple electrode layers into electrical communication with the electrode 302.

In various embodiments, the overcurrent protector 304 is selected to conduct a defibrillator pulse. In some examples, the overcurrent protector 304 is selected to interrupt electrical communication to the electrode after the overcurrent protector exceeds a threshold temperature for a predetermined period of time. In some examples, the first electrode 302 is welded to the overcurrent protector 304. In some of these embodiments, first electrode 302 is resistance welded to the overcurrent protector.

The device 300 includes a second electrode 312 disposed in the capacitor case. In various examples, the electrode 302 is anodic, and the second electrode 312 is cathodic. In various embodiments, one or more separators 310 are disposed between the electrode 302 and the second electrode 312. In some embodiments, separator 310 is used to maintain space between the electrode 302 and a second electrode 312. Separator contemplated includes Kraft paper. Some examples include one or more layers of 0.0005 inch thick Kraft paper, although the present subject matter is not so limited and other separators are used in additional embodiments. In some examples, at least two electrodes of the plurality of electrodes 306 are stacked against one another and abutting one another. In some of these examples, two anodes are stacked together and abut one another, placing each in electrical and mechanical contact with the other.

Various embodiments include a second terminal 322 disposed on the exterior of the capacitor case and in electrical communication with the second electrode 312, with the terminal 318 and the second terminal 322 electrically isolated from one another. Some examples include an interconnect 324 to interconnect additional electrodes to the second electrode 312. In some examples, the interconnect 324 is coupled with the case 308 such that the case forms part of an electrode. In some examples, the case 308 is cathodic, but the present subject matter is not so limited.

In various embodiments, the overcurrent protector 304 is to interrupt electrical communication between the terminal 318 and the remainder 316 of the electrode. In some examples, the overcurrent protector interrupts current at a selected current level. In additional embodiments, the overcurrent protector interrupts current at a selected temperature. By extension, some embodiments select a voltage threshold over which the overcurrent protector 304 interrupts electrical conduction.

Some examples include an overcurrent protector 304 that at least partially begins a phase change during high current conditions, but is able to endure the high current conditions briefly to allow the electrode 302 to charge or discharge without a permanent current interruption due to overcurrent protector 304 melting or blowing.

FIG. 4A is a perspective view of capacitor stack with multiple overcurrent protectors, according to various embodiments. FIG. 4B is a cross section taken along line 4B-4B in FIG. 4A. Various embodiments are configured with the electrode 402 being anodic and in a stack element 406 comprising electrically interconnected anode layers. An interconnection conductor 426 interconnects multiple layers in certain examples. In some embodiments, each anode layer of the stack element 406 includes a respective overcurrent protector such as overcurrent protector 404. Each of the overcurrent protectors such as overcurrent protector 404 are configured to fail at a predetermined current level. Accordingly, interruptions by one overcurrent protector does not necessarily disable all the electrode layers of the element 406. Some capacitors include multiple elements, with each disposed in a stack with electrodes of an opposite polarity.

Figure 5A:
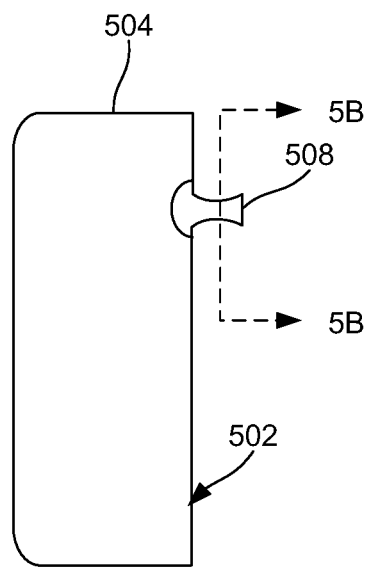
FIG. 5A is a plan view of a capacitor electrode including an overcurrent protector, according to various embodiments.
Figure 5B:
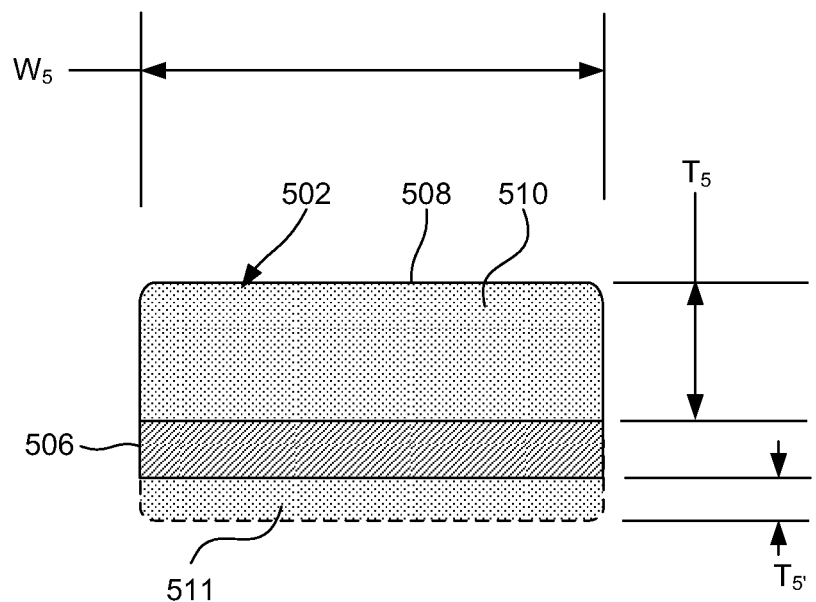
FIG. 5B is a cross section taken along line 5B-5B in FIG. 5A.

FIG. 5A is a plan view of a capacitor electrode including an overcurrent protector, according to various embodiments. FIG. 5B is a cross section taken along line 5B-5B in FIG. 5A. In various embodiments, a first electrode 502 comprises connection member 508. The connection member extends away from a main body 504 of the electrode. The connection member 508 includes a sintered material 510 in various embodiments. In some of these embodiments, the main body 504 does not include the sintered material, but the present subject matter is not so limited. In various embodiments, the sintered material 510 is disposed on a substrate 506 such as a foil, but the present subject matter extends to embodiments in which one or both of the connection member 508 and the main body 504 are sintered material without a substrate.

In various embodiments, the width $W_5$ and the thickness $T_5$ are selected such that the sintered material melts or blows when a current threshold is reached. Some examples include sintered material disposed on a main body 504 comprising the sintered portion. In additional embodiments, only the connection member 508 includes sintered material. In some examples, the width $W_5$ and the thickness $T_5$ are selected such that the sintered material melts or blows when it reaches a certain temperature. Some examples including sintering 510 and/or substrate 506 that at least partially begins a phase change during high current conditions, but is able to endure the high current conditions briefly to allow the electrode 502 to charge or discharge without a permanent current interruption due to the sintering 510 melting or blowing. Some alternative examples include a sintered portion is disposed on a foil substrate to comprise a main body, and the overcurrent protector comprises a portion of the foil substrate that is substantially free of sintered material.

Optionally, an electrode 502 includes a second portion of sintered material 511 disposed on a second surface of the substrate 506. In some embodiments, the thickness $T_{5'}$ of the second portion of sintered material 511 is substantially the same as the thickness $T_5$ of the other sintered material 510. In some embodiments, the thickness $T_{5'}$ of the second portion of sintered material 511 varies from the thickness $T_5$ of the other sintered material 510. It is understood that electrodes described herein with sintered material disposed on one side of a substrate may also be configured with a substrate having sintered material disposed on two sides of the substrate without departing from the scope of the present subject matter.

Figure 6A:
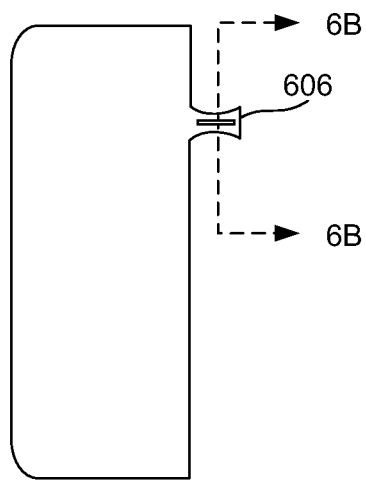
FIG. 6A is a plan view of a capacitor electrode with an overcurrent protector including a sintered portion, according to various embodiments.
Figure 6B:
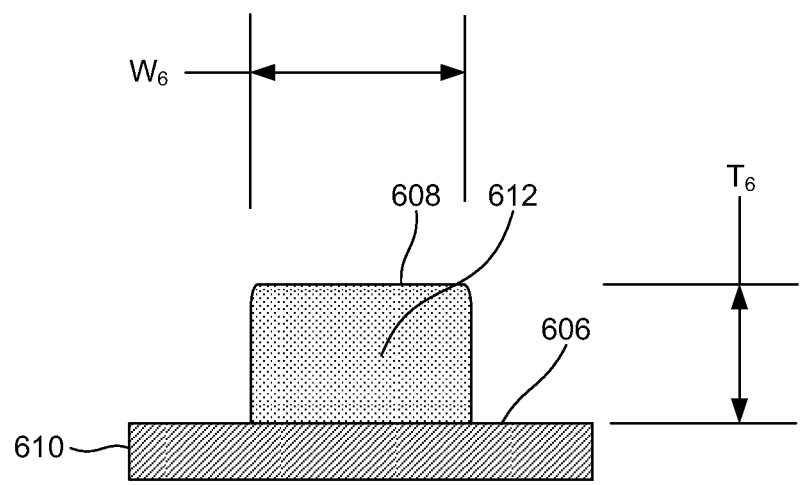
FIG. 6B is a cross section taken along the line 6B-6B in FIG. 6A.

FIG. 6A is a plan view of a capacitor electrode with an overcurrent protector including a sintered portion, according to various embodiments. FIG. 6B is a cross section taken along the line 6B-6B in FIG. 6A. The embodiment shows that sintering 608 is covering less than the entire surface of a substrate 610 of a connection member 606. The width W6 and the thickness T6 are selected to allow the connection member 606 to conduct current so long as one or more of a selected current threshold, operating temperature, voltage or time are not exceeded.

Figure 7A:
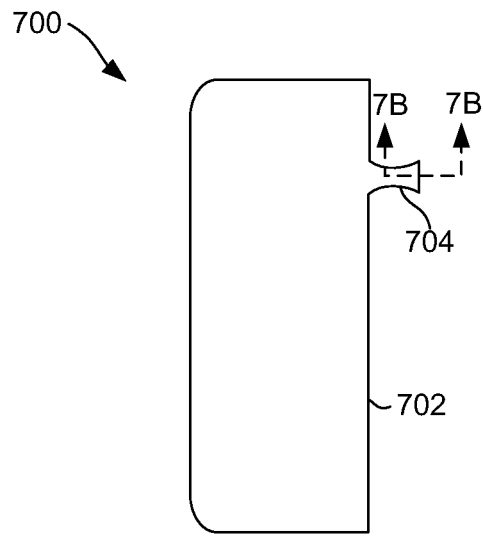
FIG. 7A is a plan view of a capacitor, according to various embodiments.
Figure 7B:
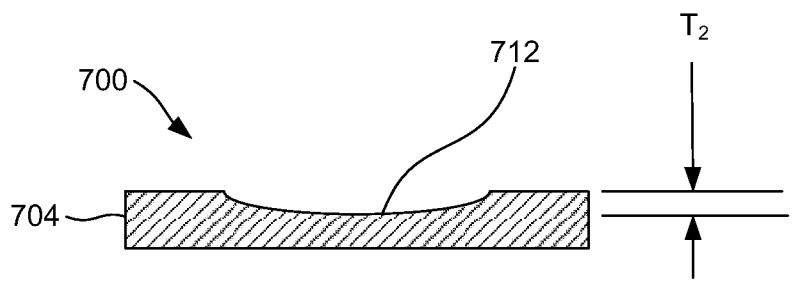
FIG. 7B is a cross section taken along the line 7B-7B in FIG. 7A.

FIG. 7A is a plan view of a capacitor, according to various embodiments. FIG. 7B is a cross section taken along the line 7B-7B in FIG. 7A. The connection member 704 includes an overcurrent protector 712 that includes an etch. In alternative embodiments, the overcurrent portion 712 includes an excised portion. Excised portions are created with lasers, die, grinders, drills, mills and the like.

Figure 7C:
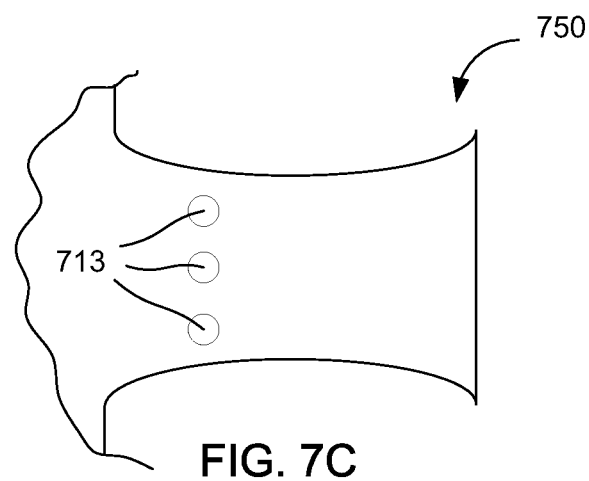
FIG. 7C shows a plan view of a connection member according to some embodiments of the present subject matter.

FIG. 7C shows a plan view of a connection member according to some embodiments of the present subject matter. The connection member 750 includes one or more holes 713. The holes 713 reduce the cross section area of the connection member, thus limiting the current capacity of the connection member 750. If excessive current is maintained through the limited cross section resulting from the holes 713, the connection member can melt and reduce or lose electrical conductivity. Size of the holes can be manipulated to provide an estimated threshold current capacity over which electrical communication is interrupted. Number of the holes can be manipulated to provide an estimated threshold current capacity over which electrical communication is interrupted. Location of the holes can be manipulated to provide an estimated threshold current capacity over which electrical communication is interrupted. Operating the connection member over the threshold current capacity results in interruption of electrical communication, thus providing over-current protection, according to various embodiments.

Figure 8A:
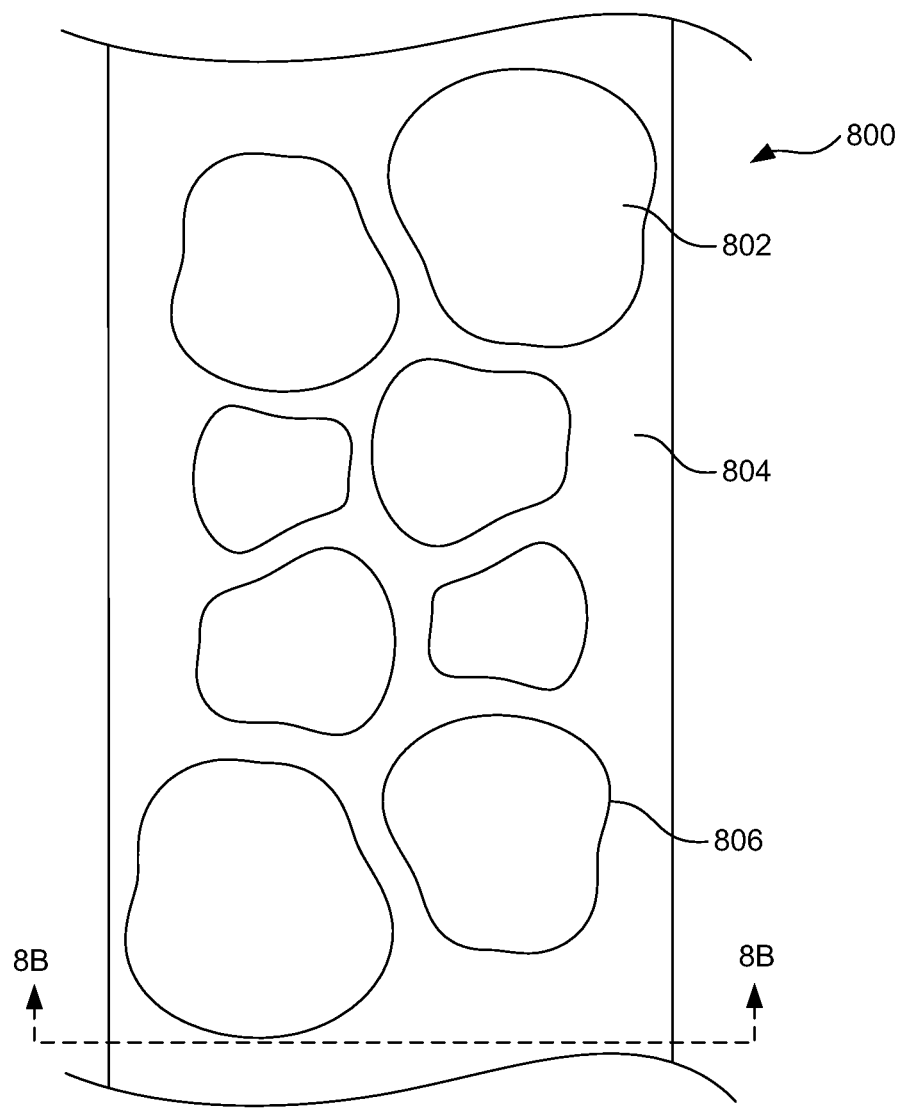
FIG. 8A is a plan view of nested sintered capacitor electrodes that have yet to be excised from a substrate, according to some embodiments.
Figure 8B:
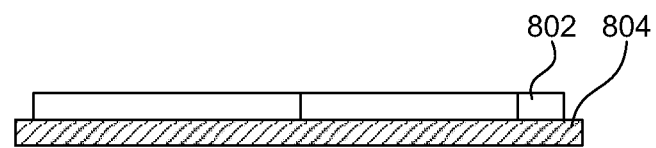
FIG. 8B is a cross section taken along the line 8B-8B in FIG. 8A.

FIG. 8A is a plan view of nested sintered capacitor electrodes that have yet to be excised from a substrate, according to some embodiments. FIG. 8B is a cross section taken along the line 8B-8B in FIG. 8A. Electrodes 802 are sintered onto a substrate 804. In various embodiments, the sintered portions are excised from the web 800. In some examples, a slug is cut on the illustrated perimeters, around them, or inside them, depending on the process used. If foils are desired, such as for use as interconnects, one or more slugs are excised around the illustrated perimeters. If no foils are desired, one or more slugs can be excised substantially at the illustrated perimeters such as perimeter 806. In some embodiments, a process cuts the slugs, such as to provide a fresh cut surface or squared edges. FIG. 8B is a front view of the electrodes and substrate of FIG. 8A and illustrates that the slugs are of a common height. The present subject matter is not so limited.

Figure 9A:
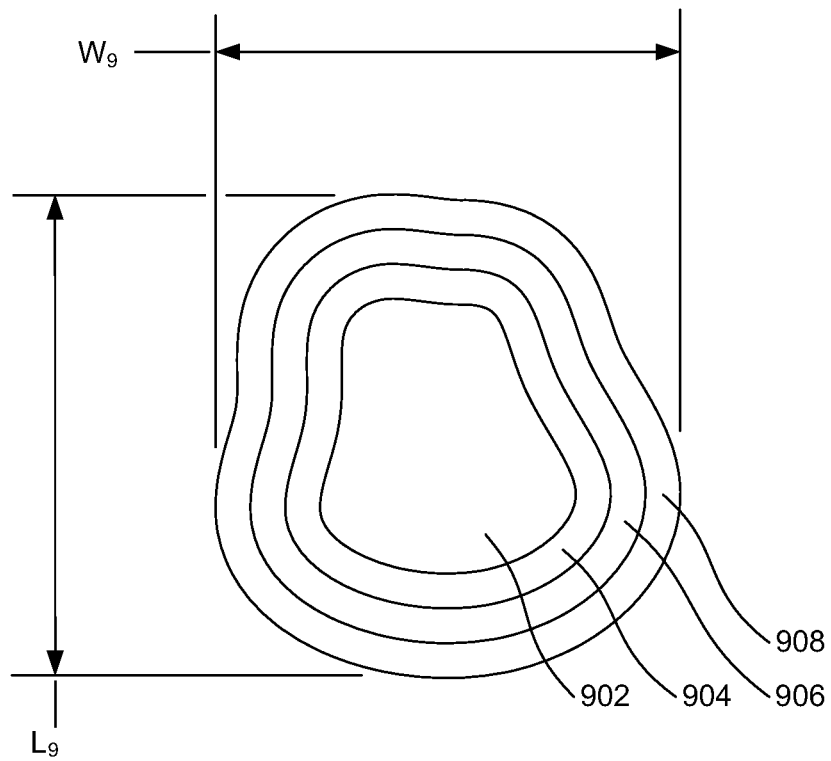
FIG. 9A is a top view of a capacitor stack, according to some embodiments.
Figure 9B:
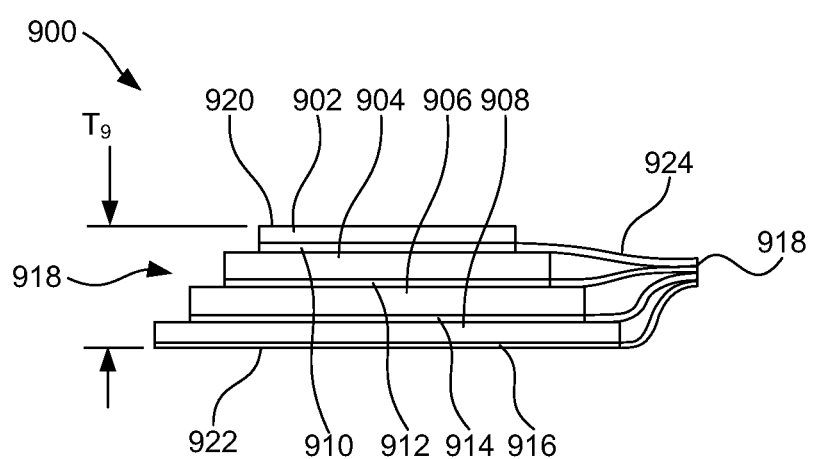
FIG. 9B is a front view of the capacitor stack of FIG. 9A, illustrating interconnects forming overcurrent protectors, according to some embodiments.

FIG. 9A is a plan view of a capacitor stack, according to some embodiments. FIG. 9B is a front view of the capacitor stack of FIG. 9A, illustrating interconnects forming one or more overcurrent protectors, according to some embodiments. In some embodiments, the stack 900 is an anode. To increase surface area of an anode, several slugs are positioned against one another and each includes a sintered portion disposed on a substrate. A first slug includes a sintered portion 902 and a substrate 910. A second slug includes a sintered portion 904 and a substrate 912. A third slug includes a sintered portion 906 and a substrate 914. A fourth slug includes a sintered portion 908 and a substrate 916. The present subject matter is not limited to stacks of sintered material and extends to stacks of other materials, such as etched material.

In various examples, the slugs are interconnected to one another mechanically and electrically. In some examples, the slugs each abut one another and are electrically connected via the abutment. In some examples, the sintered portions are welded to one another using resistance welding, such as by applying a voltage across several slugs along the axis of stacking. In some examples, several slug layers are interconnected by interconnecting respective overcurrent protectors 924, such as by adhesion, welding, fasteners, or combinations thereof. In some examples, substrates are interconnected to define an edge 918. Along the edge face, interconnection configurations include, but are not limited to, welding (including, but not limited to, laser welding), adhesion fasteners, and combinations thereof. Additionally, the substrates can be resistance welded together such as by pinching and welding.

In the illustrated configuration, a first sintered portion 902 is sintered onto a first substrate 910, and a second sintered portion 904 is sintered onto a second substrate 912. The first substrate 910 faces the second sintered portion 904 and abuts it. In additional configurations, the second slug is flipped, and the first substrate 910 abuts the second substrate 912.

In the illustrated configuration, the plurality of anodes are stacked to a stack height $T_9$, and at least two of the sintered anodes have respective widths $W_9$, perpendicular to the height $T_9$, that are substantially different such that the plurality of sintered anodes define a contoured edge 918, with the contoured edge 918 extending between a top major face 920 of a top sintered portion 902 and a bottom major face 922 of a bottom substrate 916. In some examples at least two of the sintered anodes have respective lengths $L_9$, perpendicular to the height $T_9$, that are substantially different such that the plurality of sintered anodes define a contoured edge 918, with the contoured edge 918 extending between a top major face 920 of a top sintered portion 902 and a bottom major face 922 of a bottom substrate 916. Accordingly, the top major face 920 and the bottom major face 922 have different areas. The top major face 920 and the bottom major face 922 are substantially parallel.

In another configuration, the plurality of slugs are stacked to a stack height $T_9$, and at least two of the sintered anodes have respective widths $W_9$, perpendicular to the height $T_9$, that are substantially equal such that the plurality of sintered anodes define a side surface that is substantially parallel to the height $T_9$. In the illustrated configuration, the top major face 920 and the bottom major face 922 are shaped similarly, but in additional embodiments, they are not.

Figure 10:
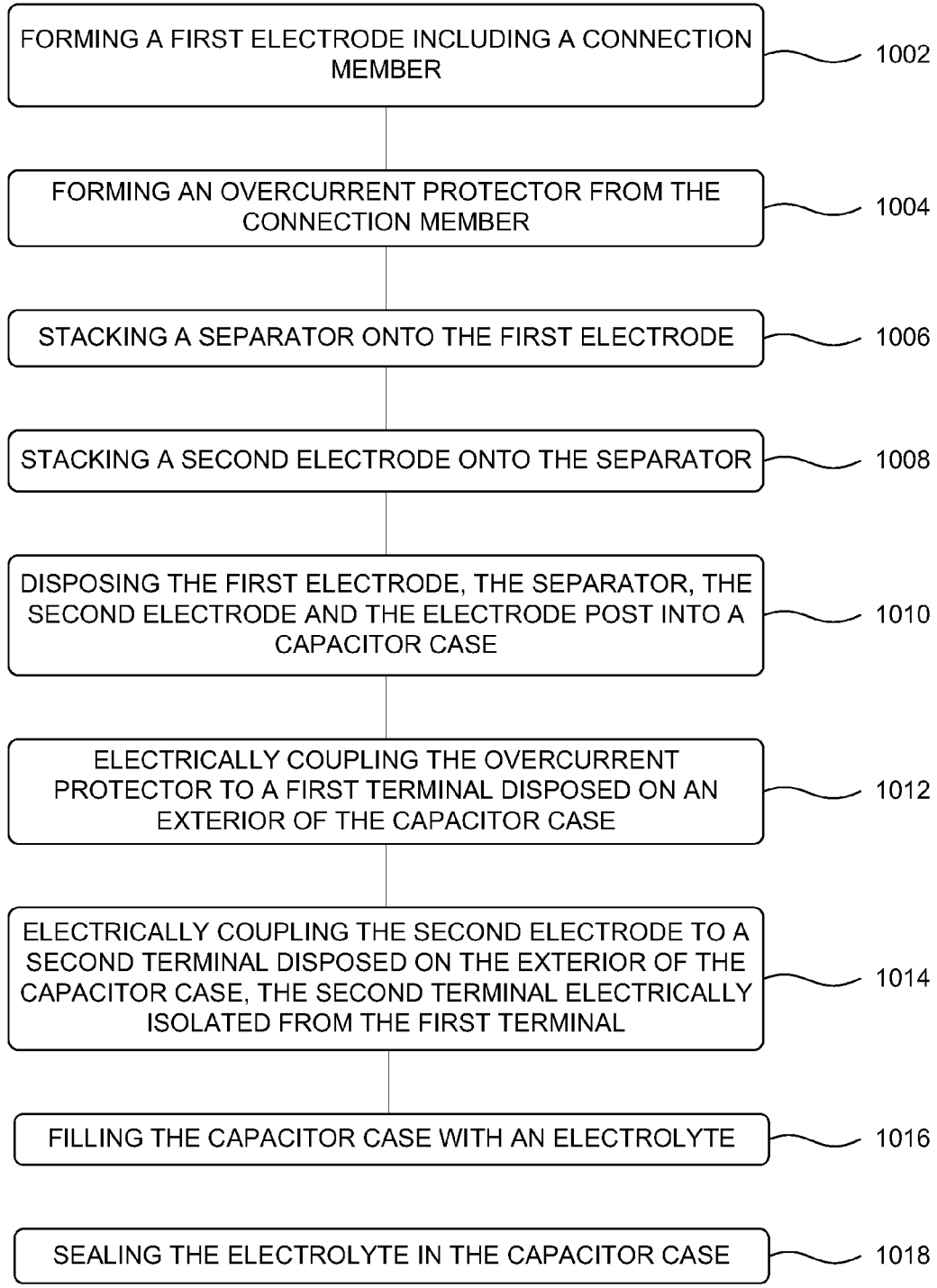
FIG. 10 is a method of making a capacitor including overcurrent protection, according to some embodiments.

FIG. 10 is a method of making a capacitor including overcurrent protection, according to some embodiments. At 1002, the method includes forming a first electrode including a connection member comprising an overcurrent protector. At 1004, the method includes coupling the overcurrent protector to a first electrode. At 1006, the method includes stacking a separator onto the first electrode. At 1008, the method includes stacking a second electrode onto the separator. At 1010, the method includes disposing the first electrode, the separator, the second electrode and overcurrent protector into a capacitor case. At 1012, the method includes electrically coupling the first electrode and the electrode pose to a first terminal disposed on an exterior of the capacitor case. At 1014, the method includes electrically coupling the second electrode to a second terminal disposed on the exterior of the capacitor case, the second terminal electrically isolated from the first terminal. At 1016, the method includes filling the capacitor case with an electrolyte. At 1018, the method includes sealing the electrolyte in the capacitor case.

In some optional embodiments, the method includes forming the first electrode by sintering material onto a foil substrate, and forming the overcurrent protector out of the foil substrate. Additionally, some embodiments include forming the overcurrent protector includes excising the foil substrate.

Some embodiments include a method of determining a maximum current conduction rate for a capacitor stack to maintain the capacitor stack below a predetermined temperature threshold. The method includes selecting a overcurrent protector to blow when the capacitor stack is above the predetermined temperature threshold. The method includes charging a capacitor stack by conducing energy through the overcurrent protector at a current that is below a predetermined current. The method additionally includes discharging the capacitor stack through the overcurrent protector at a discharge current that is below the predetermined current.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An apparatus, comprising:
  a capacitor case sealed to retain electrolyte;
  at least one electrode disposed in the capacitor case, the at least one electrode comprising an overcurrent protector formed from a portion of the electrode, wherein the at least one electrode comprises a sheet with a main body comprising a sintered portion, and a connection member extending away from the main body, the connection member comprising the overcurrent protector;
  a conductor coupled to the overcurrent protector and in electrical communication with remainder of the electrode, the conductor sealingly extending through the capacitor case to a terminal disposed on an exterior of the capacitor case;
  a second electrode disposed in the capacitor case;
  a separator disposed between the electrode and the second electrode; and
  a second terminal disposed on the exterior of the capacitor case and in electrical communication with the second electrode, with the terminal and the second terminal electrically isolated from one another,
  wherein the overcurrent protector is to interrupt electrical communication between the terminal and the remainder of the electrode at a selected current level.

2. The apparatus of claim 1, wherein the overcurrent protector includes the sintered portion.

3. The apparatus of claim 1, wherein the sintered portion is disposed on a foil substrate, and the overcurrent protector comprises a portion of the foil substrate that is substantially free of sintered material.

4. The apparatus of claim 1, wherein the overcurrent protector is selected to conduct a defibrillator pulse.

5. The apparatus of claim 1, wherein the overcurrent protector is selected to interrupt electrical communication to the electrode after the overcurrent protector exceeds a threshold temperature for a predetermined period of time.

6. The apparatus of claim 1, wherein the overcurrent protector comprises another sintered portion disposed on the connection member.

7. The apparatus of claim 6, wherein the at least one electrode is resistance welded to the overcurrent protector.

8. The apparatus of claim 1, wherein the overcurrent protector comprises one or more holes termed in the connection member.

9. A system, comprising:
  a hermetically seated device housing;
  a battery disposed in the hermetically sealed device housing;
  a capacitor disposed in the hermetically seated device housing, the capacitor comprising:
    a capacitor case sealed to retain electrolyte;

at least one electrode disposed in the capacitor case, the at least one electrode comprising an overcurrent protector formed from a portion of the electrode, wherein the at least one electrode comprises a sheet with a main body comprising a sintered portion, and a connection member extending away from the main body, the connection member comprising the overcurrent protector;

a conductor coupled to the overcurrent protector and in electrical communication with a remainder of the electrode, the conductor sealingly extending through the capacitor case to a terminal disposed on an exterior of the capacitor case;

a second electrode disposed in the capacitor case;

a separator disposed between the electrode and the second electrode; and a second terminal disposed on the exterior of the capacitor case and in electrical communication with the second electrode, with the terminal and the second terminal electrically isolated from one another, wherein the overcurrent protector is to interrupt electrical communication between the terminal and the remainder of the electrode at a selected current level, and an electronic cardiac rhythm management circuit coupled to the battery and the capacitor and adapted to charge the capacitor with the battery and to discharge the capacitor to provide a therapeutic defibrillation pulse.

10. The system of claim 9, wherein at least two electrodes including the at least one electrode and the second electrode are stacked against one another and abutting one another.

11. The system of claim 9, wherein the case includes a dish portion and lid portion, with the overcurrent protector fixed to the dish portion.

12. The system of claim 9, wherein the electronic cardiac rhythm management circuit comprises a defibrillator circuit.

13. The system of claim 12, wherein the at least one electrode is part of an anode, and the second electrode is part of a cathode, and the defibrillator circuit is to entirely discharge the anode and the cathode to provide a single therapeutically effective defibrillator pulse.

14. The system of claim 13, wherein the anode and the cathode are sized to deliver a defibrillation pulse of approximately 50 joules.

15. The system of claim 13, wherein the anode and the cathode are sized and packaged to deliver a defibrillation pulse of approximately 50 joules.

16. The system of claim 9, wherein the sintered portion is disposed on a foil substrate, and the overcurrent protector comprises a portion of the foil substrate that is substantially free of sintered material.

17. The system of claim 9, wherein the overcurrent protector comprises one or more holes formed in the connection member.

18. A method of constructing a capacitor, comprising:
forming a first electrode including a connection member;
forming an overcurrent protector from the connection member;
stacking a separator onto the first electrode;
stacking a second electrode onto the separator;
disposing the first electrode, the separator, the second electrode and overcurrent protector into a capacitor case;
electrically coupling the overcurrent protector to a first terminal disposed on an exterior of the capacitor case;
electrically coupling the second electrode to a second terminal disposed on the exterior of the capacitor case, the second terminal electrically isolated from the first terminal;
filling the capacitor case with an electrolyte;
sealing the electrolyte in the capacitor case; and
forming the first electrode by sintering material onto a foil substrate, and forming the overcurrent protector out of the foil substrate.

19. The method of claim 18, wherein forming the overcurrent protector includes excising the foil substrate.

\* \* \* \* \*